(12) United States Patent
Clausen et al.

(10) Patent No.: US 7,891,258 B2
(45) Date of Patent: *Feb. 22, 2011

(54) METHOD OF MEASURING THE PERFORMANCE OF A PROSTHETIC FOOT

(75) Inventors: Arinbjorn Viggo Clausen, Reykjavik (IS); Kim De Roy, Reykajvik (IS)

(73) Assignee: Össur hf (IS)

( * ) Notice: Subject to any disclaimer, the term of this patent is extended or adjusted under 35 U.S.C. 154(b) by 0 days.

This patent is subject to a terminal disclaimer.

(21) Appl. No.: 12/538,074

(22) Filed: Aug. 7, 2009

(65) Prior Publication Data

US 2009/0293641 A1    Dec. 3, 2009

Related U.S. Application Data

(63) Continuation of application No. 11/184,011, filed on Sep. 20, 2004, now Pat. No. 7,581,454, which is a continuation-in-part of application No. 10/944,436, filed on Sep. 17, 2004, now Pat. No. 7,347,877.

(60) Provisional application No. 60/590,717, filed on Jul. 23, 2004, provisional application No. 60/575,142, filed on May 28, 2004.

(51) Int. Cl.
  *G01D 7/00*    (2006.01)
(52) U.S. Cl. .................................. 73/862.046
(58) Field of Classification Search ........................ None
  See application file for complete search history.

(56) References Cited

U.S. PATENT DOCUMENTS

| 25,238 A | 8/1859 | Bly |
|---|---|---|
| 53,931 A | 4/1866 | Weston et al. |
| 56,983 A | 8/1866 | Nicholas |
| 57,666 A | 9/1866 | Bly |
| 368,580 A | 8/1887 | Frees |
| 487,697 A | 12/1892 | Ehle |
| 534,198 A | 2/1895 | Chapman |
| 619,731 A | 2/1899 | Doerflinger et al. |

(Continued)

FOREIGN PATENT DOCUMENTS

DE    817186    10/1951

(Continued)

OTHER PUBLICATIONS

Ohio Willow Wood Company: Carbon Copy System 111 brochure, 5 pages; believed to have been available prior to May, 2004.

(Continued)

*Primary Examiner*—Andre J Allen
(74) *Attorney, Agent, or Firm*—Knobbe, Martens, Olson & Bear LLP (57) ABSTRACT

A method of measuring the performance of a prosthetic foot includes obtaining a pressure distribution of the prosthetic foot during a motion of the prosthetic foot and determining whether the pressure distribution falls within a preselected range of performance values for the prosthetic foot. The pressure distribution comprises a trajectory illustrating the progression of a center of pressure of the prosthetic foot during motion. A prosthetic foot can also be designed to approximate a pressure distribution corresponding to a preselected range of performance values.

25 Claims, 6 Drawing Sheets

U.S. PATENT DOCUMENTS

| | | |
|---|---|---|
| 808,296 A | 12/1905 | Merrick |
| 809,876 A | 1/1906 | Wilkins |
| 817,340 A | 4/1906 | Rosenkranz |
| 2,183,076 A | 12/1939 | Kaiser |
| 2,197,093 A | 4/1940 | Campbell |
| 2,315,795 A | 4/1943 | Johnson et al. |
| 2,357,893 A | 9/1944 | Harrington |
| 2,594,945 A | 4/1952 | Lucas et al. |
| 2,692,392 A | 10/1954 | Bennington et al. |
| 2,731,645 A | 1/1956 | Woodall |
| 3,551,914 A | 1/1971 | Woodall |
| 3,784,988 A | 1/1974 | Trumpler |
| 3,874,004 A | 4/1975 | May |
| 4,007,497 A | 2/1977 | Haupt |
| 4,360,931 A | 11/1982 | Hampton |
| 4,387,472 A | 6/1983 | Wilson |
| 4,547,913 A | 10/1985 | Phillips |
| 4,718,913 A | 1/1988 | Voisin |
| 4,822,363 A | 4/1989 | Phillips |
| 4,892,553 A | 1/1990 | Prahl |
| 4,892,554 A | 1/1990 | Robinson |
| 4,959,073 A | 9/1990 | Merlette |
| 5,019,109 A | 5/1991 | Volsin |
| 5,037,444 A | 8/1991 | Phillips |
| 5,062,859 A | 11/1991 | Naeder |
| 5,116,384 A | 5/1992 | Wilson et al. |
| 5,139,525 A | 8/1992 | Kristinsson |
| 5,156,631 A | 10/1992 | Merlette |
| 5,181,932 A | 1/1993 | Phillips |
| 5,181,933 A | 1/1993 | Phillips |
| 5,219,365 A | 6/1993 | Sabolich |
| 5,258,039 A | 11/1993 | Goh et al. |
| 5,290,319 A | 3/1994 | Phillips |
| 5,376,133 A | 12/1994 | Gramnas |
| 5,376,141 A | 12/1994 | Phillips |
| 5,387,246 A | 2/1995 | Phillips |
| 5,443,527 A | 8/1995 | Wilson |
| 5,443,529 A | 8/1995 | Phillips |
| 5,509,938 A | 4/1996 | Phillips |
| 5,653,767 A | 8/1997 | Allen et al. |
| 5,701,686 A | 12/1997 | Berr et al. |
| 5,728,177 A | 3/1998 | Phillips |
| 5,800,569 A | 9/1998 | Phillips |
| 5,897,594 A | 4/1999 | Martin et al. |
| 5,899,944 A | 5/1999 | Phillips |
| 5,941,913 A | 8/1999 | Woolnough et al. |
| 5,957,981 A | 9/1999 | Gramnas |
| 5,993,488 A | 11/1999 | Phillips |
| 6,071,313 A | 6/2000 | Phillips |
| 6,099,572 A | 8/2000 | Mosier et al. |
| 6,129,766 A | 10/2000 | Johnson et al. |
| 6,155,120 A * | 12/2000 | Taylor ............... 73/862.046 |
| 6,165,227 A | 12/2000 | Phillips |
| 6,206,934 B1 | 3/2001 | Phillips |
| 6,216,545 B1 * | 4/2001 | Taylor ............... 73/862.046 |
| 6,241,776 B1 | 6/2001 | Christensen |
| 6,261,324 B1 | 7/2001 | Merlette |
| 6,280,479 B1 | 8/2001 | Phillips |
| 6,350,286 B1 | 2/2002 | Atkinson et al. |
| 6,387,134 B1 | 5/2002 | Parker et al. |
| 6,398,818 B1 | 6/2002 | Merlette et al. |
| 6,402,790 B1 | 6/2002 | Celebi |
| 6,443,995 B1 | 9/2002 | Townsend et al. |
| 6,663,673 B2 | 12/2003 | Christensen |
| 6,712,860 B2 | 3/2004 | Rubie et al. |
| 6,719,807 B2 | 4/2004 | Harris |
| 6,767,370 B1 | 7/2004 | Mosier et al. |
| 6,793,683 B1 | 9/2004 | Laghi |
| 6,899,737 B1 | 5/2005 | Phillips |
| 6,969,408 B2 | 11/2005 | Lecomte et al. |
| 7,347,877 B2 | 3/2008 | Clausen et al. |
| 2002/0013628 A1 | 1/2002 | Harris |
| 2002/0040249 A1 | 4/2002 | Phillips |
| 2002/0087216 A1 | 7/2002 | Atkinson et al. |
| 2002/0116072 A1 | 8/2002 | Rubie et al. |
| 2002/0143408 A1 | 10/2002 | Townsend et al. |
| 2002/0183860 A1 | 12/2002 | Wilkinson |
| 2002/0193707 A1 * | 12/2002 | Atlas et al. ............ 600/595 |
| 2003/0093158 A1 | 5/2003 | Phillips |
| 2003/0120353 A1 | 6/2003 | Christensen |
| 2004/0064195 A1 | 4/2004 | Herr |
| 2004/0068327 A1 | 4/2004 | Christensen |
| 2004/0112138 A1 * | 6/2004 | Knirck et al. ........... 73/754 |
| 2004/0122529 A1 | 6/2004 | Townsend et al. |
| 2004/0162623 A1 | 8/2004 | Phillips |
| 2004/0181289 A1 | 9/2004 | Bedard et al. |
| 2004/0225376 A1 | 11/2004 | Townsend et al. |
| 2005/0038524 A1 | 2/2005 | Jonsson et al. |
| 2005/0038525 A1 | 2/2005 | Doddroe et al. |
| 2005/0107889 A1 * | 5/2005 | Bedard et al. ............ 623/24 |
| 2005/0137717 A1 | 6/2005 | Gramnas et al. |
| 2005/0267603 A1 | 12/2005 | Lecomte et al. |
| 2006/0069450 A1 | 3/2006 | McCarvill et al. |
| 2007/0027557 A1 | 2/2007 | Jonsson et al. |

FOREIGN PATENT DOCUMENTS

| | | |
|---|---|---|
| DE | 834884 | 3/1952 |
| DE | 838480 | 8/1952 |
| DE | 695224 | 11/1954 |
| DE | 024763 | 1/1955 |
| DE | 924230 | 2/1955 |
| DE | 832473 | 2/1957 |
| DE | 300043 | 4/1964 |
| DE | 1491182 | 7/1969 |
| DE | 1941762 | 3/1971 |
| DE | 298 20 904 | 4/1999 |
| EP | 0 401 864 | 9/1989 |
| EP | 0 940 129 | 11/1992 |
| EP | 1 149 568 | 10/2001 |
| FR | 661071 | 7/1929 |
| FR | 1213026 | 3/1960 |
| FR | 2 658 717 | 8/1991 |
| GB | 117547 | 8/1918 |
| GB | 120462 | 11/1918 |
| GB | 621576 | 4/1949 |
| GB | 625528 | 6/1949 |
| GB | 1371996 | 10/1974 |
| KR | 2001/0055393 | 7/2001 |
| SU | 1454449 | 1/1989 |
| SU | 1600759 | 10/1990 |
| SU | 1700759 | 12/1991 |
| WO | WO 88/06431 | 9/1988 |
| WO | WO 93/04645 | 3/1993 |
| WO | WO 94/18914 | 9/1994 |
| WO | WO 96/04869 | 2/1996 |
| WO | WO 98/53769 | 12/1998 |
| WO | WO 99/52476 | 10/1999 |
| WO | WO 00/27317 | 5/2000 |
| WO | WO 02/02034 | 1/2002 |
| WO | WO 02/051342 | 7/2002 |
| WO | WO 2004/032809 | 4/2004 |
| WO | PCT/US2004/025554 | 8/2004 |
| WO | WO 2005/048887 | 6/2005 |

OTHER PUBLICATIONS

Commercial Ad for College Park Venture Prosthetic Foot; http:--www.college-park.com-assets-pdf-VentureInfoSheets.pdf, 2003, and www.college-park.com-CPStore-ProductInfoVenture.asp; available before Aug. 15, 2003.

Freedom Innovations FS2000 LP product; http:--www.freedom-innovations.com-html-details.html, 2003; available before Aug. 15, 2003.

OSSUR Allurion product; http:--www.ossur.com-template1.asp-?pageid=84 and product catalog pp. 146-149; available before Aug. 15, 2003.

OSSUR Elation product; http:--www.ossur.com-template1.asp-?pageid=263 and product catalog pp. 193-196; available before Aug. 15, 2003.

International Search Report dated Apr. 28, 2006; PCT-2005-017884 filed May 20, 2005.

International Search Report dated May 27, 2005; PCT-US2004-025554 filed Jun. 8, 2004.

Otto Bock—Axtion product; http:--www.ottobockus.com-products-lower limb prosthetics-axtion.asp; believed to have been released May, 2004.

The Quantum Foot (Hosmer Dorrance Corporation), no date but published more than one year prior to Nov. 12, 2004.

English translation of IPOS, DE 299 12832 U1, published in Nov. 2000.

English translation of KR 2000-002059A, notification date is Jan. 15, 2000.

English translation of Bernhardsson, SE 9400380-3A, published in Aug. 1995.

Office Action mailed Apr. 8, 2008 in U.S. Appl. No. 10/987,940.

Office Action mailed Nov. 13, 2008 in U.S. Appl. No. 10/987,940.

Office Action mailed Apr. 3, 2009 in U.S. Appl. No. 10/987,940.

Office Action mailed Nov. 27, 2009 in U.S. Appl. No. 10/987,940.

* cited by examiner

METHOD OF MEASURING THE PERFORMANCE OF A PROSTHETIC FOOT

This application is a continuation of U.S. application Ser. No. 11/184,011, filed Sep. 20, 2004, which is a continuation-in-part of U.S. application Ser. No. 10/944,436, filed Sep. 17, 2004, now U.S. Pat. No. 7,347,877. U.S. application Ser. No. 11/184,011 also claims priority to U.S. Provisional Patent Application No. 60/575,142, filed May 28, 2004, and U.S. Provisional Patent Application No. 60/590,717, filed Jul. 23, 2004.

BACKGROUND OF THE INVENTION

1. Field of the Invention

The present embodiments generally relate to prosthetic feet, and more particularly, to methods of measuring the performance of prosthetic feet.

2. Description of the Related Art

Methods for measuring the performance of prosthetic feet are known in the art. Conventional methods include comparing the gait characteristics of different prosthetic foot designs, as well as comparing the gait characteristic of a prosthetic foot with the natural gait of a human foot. However, it is often difficult to illustrate the performance of prosthetic foot designs based on said methods, or to provide a user with a simple and easy to understand performance comparison of prosthetic foot designs. Accordingly, a need exists for a simpler, easier to understand method for measuring and illustrating the performance of a prosthetic foot.

SUMMARY OF THE INVENTION

In accordance with one embodiment disclosed herein, a method of measuring the performance of a prosthetic foot is provided. The method comprises the steps of obtaining a pressure distribution of a prosthetic foot measured as the foot is in motion and determining whether the pressure distribution falls within a preselected range of performance values for the prosthetic foot.

In accordance with another embodiment, a method for designing a prosthetic foot is provided. The method comprises obtaining a pressure distribution of at least a portion of a prosthetic foot that is in motion and designing the prosthetic foot to approximate a desired pressure distribution corresponding to a preselected range of rollover performance values.

In accordance with still another embodiment, a method for illustrating the performance of a prosthetic foot is provided. The method comprises obtaining a pressure distribution of a prosthetic foot while it's in motion and displaying the pressure distribution on an image of the prosthetic foot to demonstrate the performance of the foot.

In yet another embodiment, a method of comparing the performance of prosthetic feet is provided. The method comprises obtaining a pressure distribution of a first prosthetic foot, where the pressure distribution defines a first trajectory. The method also comprises obtaining a pressure distribution of a second prosthetic foot, where the pressure distribution defines a second trajectory. The method also comprises comparing the first and second trajectories and determining which of said first and second prosthetic feet has a superior performance based on said comparison.

In still another embodiment, a method of comparing the performance of a prosthetic foot and a human foot is provided. The method comprises obtaining a pressure distribution of a human foot, the pressure distribution defining a first trajectory. The method additionally comprises obtaining a pressure distribution of a prosthetic foot, the pressure distribution defining a second trajectory. The method also comprises comparing the first and second trajectories and determining a performance rating for the prosthetic foot based on said comparison.

DETAILED DESCRIPTION OF THE PREFERRED EMBODIMENT

Figure 1:
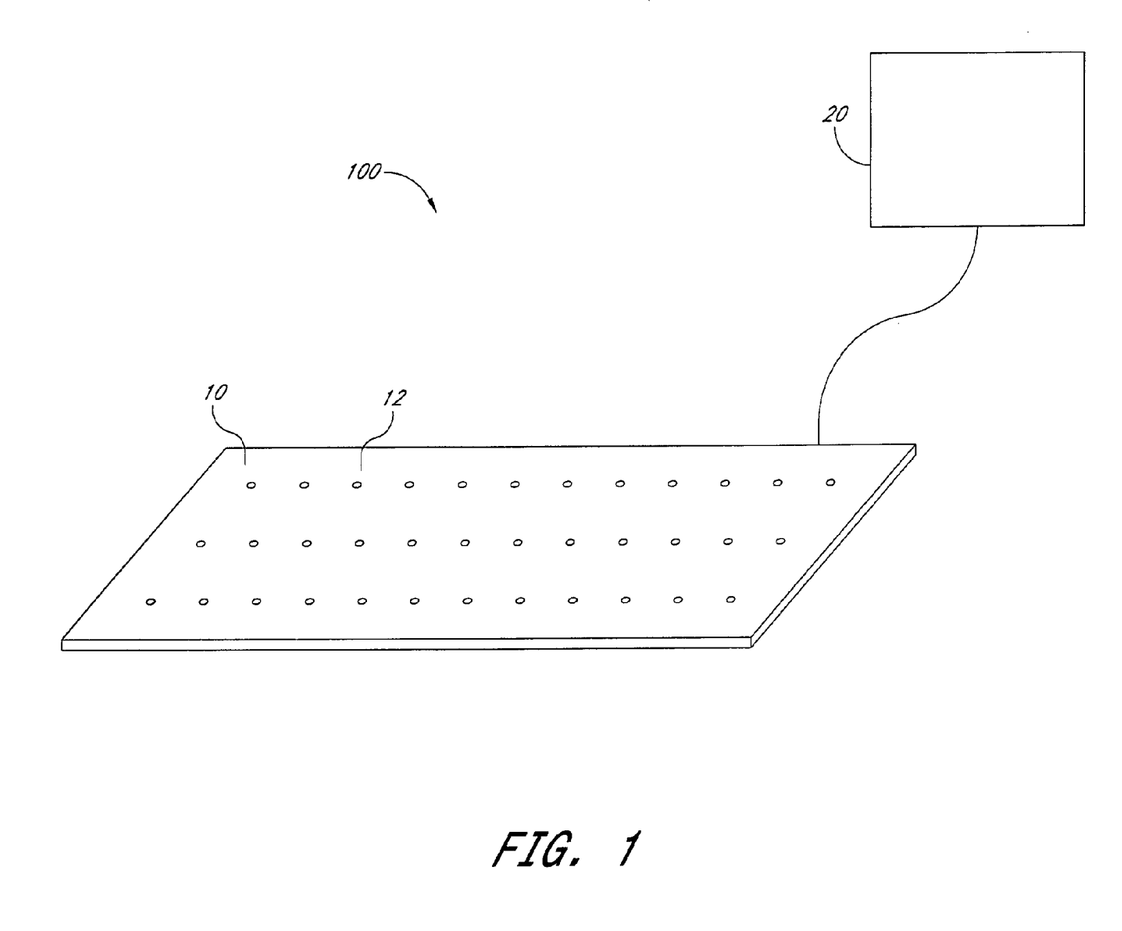
FIG. 1 is a schematic of a system for measuring the performance of a prosthetic foot.

FIG. 1 illustrates a system 100 for measuring the performance of a prosthetic foot or other leg support device. In one embodiment, the system 100 can be used to measure the performance of an orthotic device disposed on a human foot, such as a foot or ankle brace. In still another embodiment, the system 100 can be used to measure the performance of a prosthetic knee. Accordingly, the scope of the invention herein disclosed should not be limited by the particular disclosed embodiments described below. Moreover, the embodiments below are not limited to prosthetic feet but can be applied to other leg support devices, including orthotic devices.

As shown in FIG. 1, The system 100 preferably comprises a surface 10, wherein the surface 10 includes a plurality of sensors 12 configured to sense a force exerted thereon by the prosthetic foot. The sensors 12 communicate with a computer 20, which obtains the sensed forces from the sensors 12. In one preferred system, the surface 10 comprises a Footscan® plate and the computer 20 comprises a Footscan® 3D box, both by RS Scan International of Belgium. However, the system 100 can comprise any combination of components capable of obtaining the pressure distribution of a prosthetic foot or other leg support device, as discussed below. Another such system is disclosed in U.S. Pat. No. 6,505,522, issued on Jan. 14, 2003 to Wilssens, the contents of which are hereby incorporated by reference in their entirety and should be considered a part of this specification.

Figure 2:
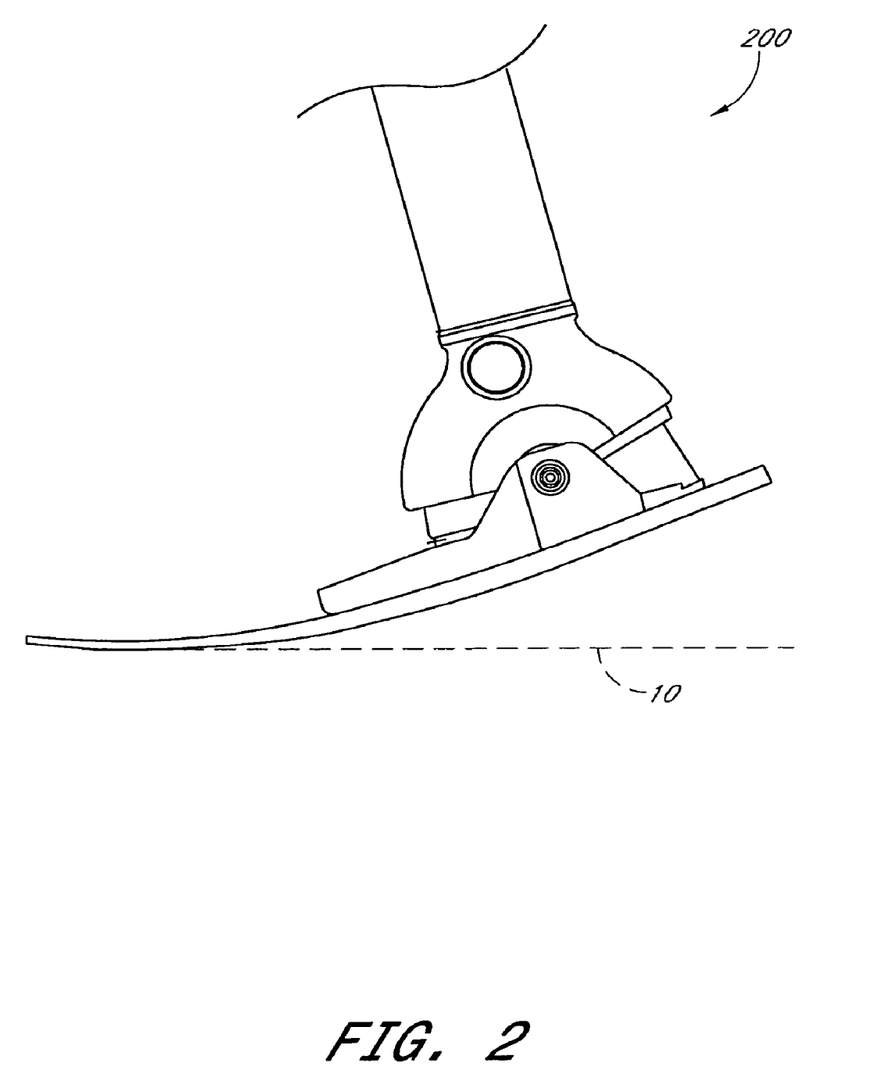
FIG. 2 is a side view of a prosthetic foot moving over a surface used to measure the performance of the prosthetic foot.

In a preferred embodiment, the surface 10 comprises a plank 10 upon which a prosthetic foot 200 is placed to obtain the pressure distribution of the prosthetic foot 200, as shown in FIG. 2. In the illustrated embodiment, the prosthetic foot 200 is an Elation™ foot by Ossur of Iceland. Preferably, the prosthetic foot 200 is moved over the plank 10 to obtain the pressure distribution while the prosthetic foot 200 is in motion. For example, a user wearing the prosthetic foot 200 can move over the plank 10 in a posterior-anterior fashion between a heel-strike and a toe-off position of the prosthetic foot 200. As used herein, posterior refers to the rear portion or back of the prosthetic foot 200 and anterior refers to the forward portion of front of the prosthetic foot 200. The posterior-anterior motion of the prosthetic foot 200 during use is also known as the rollover of the prosthetic foot 200.

Continuing with FIG. 2, in one embodiment the user can move over the plank 10 using a substantially normal walking stride. In another embodiment, the user can move over the plank 10 using a running or jogging stride. In the illustrated embodiment, the prosthetic foot 200 is shown during a toe-off position on the plank 10. One of ordinary skill in the art will recognize that the prosthetic foot 200 illustrated in FIG. 2 depicts one prosthetic foot design and that the embodiments disclosed herein are not limited to the prosthetic foot designs disclosed.

Figure 3:
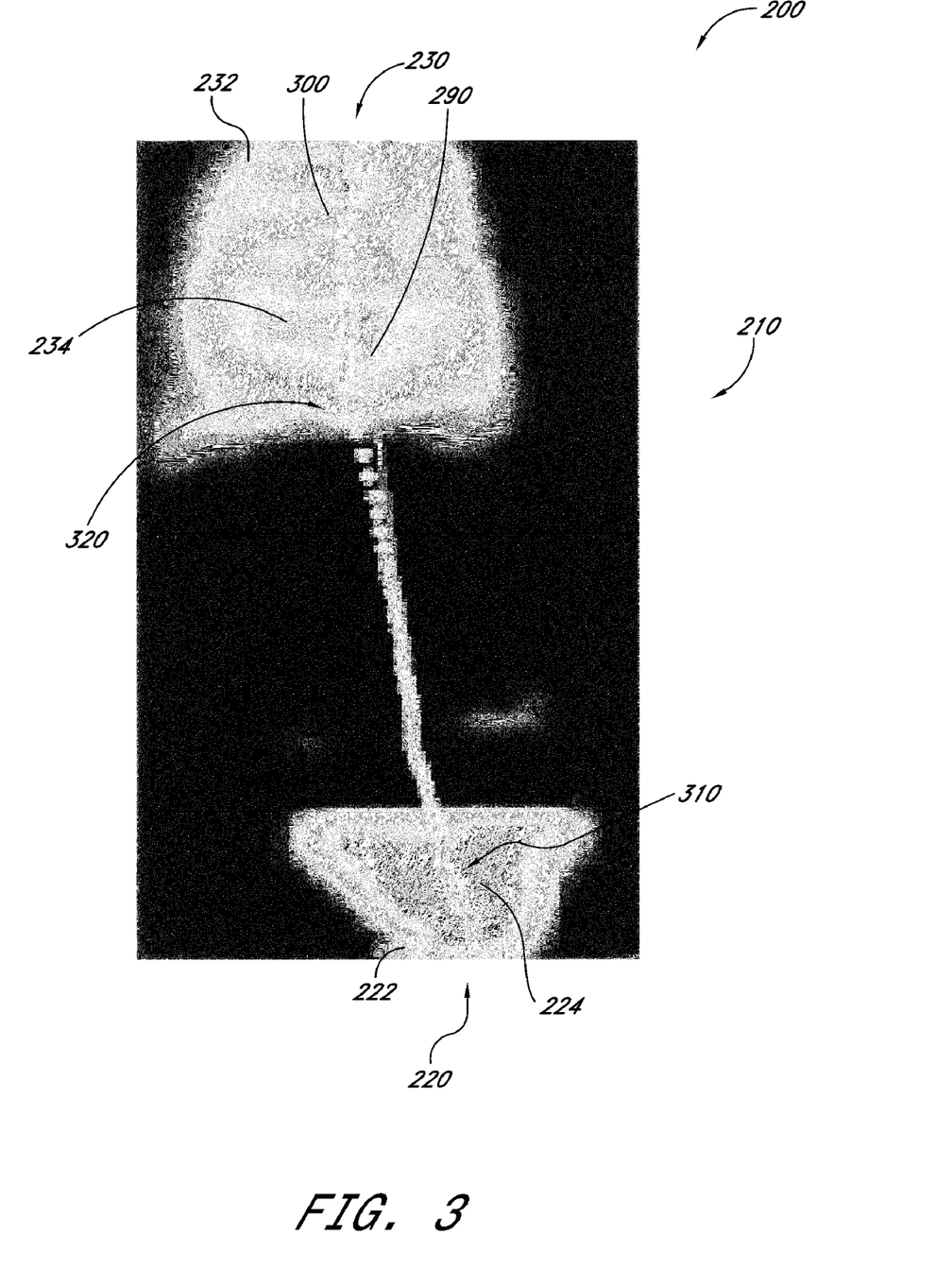
FIG. 3 is an image of a prosthetic foot and a pressure distribution of the foot.

With reference to FIGS. 1-3, the computer 20 preferably collects the force data from the sensors 12 and calculates a corresponding pressure exerted by the prosthetic foot 200 at each of the sensors 12 via a suitable software program. The pressure corresponds to the force exerted by the prosthetic foot 200 on one of the sensors 12 over an area of the foot 200 disposed over said sensor 12. Accordingly, the center of pressure corresponds to a geometric indication of the pressure exerted over said area. For example, where the prosthetic foot 200 exerts a uniform force over the area disposed on the sensor 12, the center of pressure would be the geometric center of the area. However, where the exerted force is greater on a first portion of the area than a second portion of the area, the center of pressure would instead be disposed closer to said first portion, not at the geometric center of the area. The center of pressure values obtained during the motion of the prosthetic foot 200 over the surface 10 collectively define a pressure distribution of the foot.

In one embodiment, the computer 20 preferably generates an image of the pressure distribution using said software. In one embodiment, the image is a static image, such as a photograph. In another embodiment, the image is a dynamic image showing the progression of the center of pressure of the prosthetic foot 200 as the prosthetic foot 200 moves over the surface 10.

As shown in FIG. 3, the pressure distribution comprises a trajectory of the center of pressure of the prosthetic foot 200 during the posterior-anterior motion or rollover of the prosthetic foot 200. In one embodiment the computer 20 displays the pressure distribution and includes an image of the prosthetic foot 200, such as an image of a sole 210 of the prosthetic foot 200, as shown in FIG. 3. In the illustrated embodiment, the prosthetic foot 200 is a left foot model of the LP Vari-Flex® by Ossur, as described in U.S. patent application Ser. No. 10/642,125, filed Aug. 15, 2003, which is hereby incorporated by reference in its entirety and should be considered a part of this specification. However, as discussed above, an image of the right foot model, and its associated pressure distribution, can also be displayed, as desired by the user. In another embodiment, the force or pressure distribution data collected by the computer 20 can be transferred to a separate device and used to generate the image of the pressure distribution and/or prosthetic foot 200.

As shown in FIG. 3, in one embodiment the image of the sole 210 also illustrates the degree of pressure exerted by the prosthetic foot 200 at different locations of the sole 210 during the posterior-anterior motion. For example, the pressure level can be illustrated using a spectrum of color with areas of lower pressure indicated with one shade or pattern, and areas of a higher pressure indicated with another shade or pattern. In the illustrated embodiment, a lower pressure is illustrated by a lighter color, such as green, along a periphery 222 of a posterior end 220 of the prosthetic foot 200. In contrast, a higher pressure is illustrated by a darker color, such as a red, at a central portion 224 of the posterior end 220. Likewise, in the illustrated embodiment, areas of lower pressure are shown at a periphery 232 of an anterior end 230 of the prosthetic foot 200, whereas areas of higher pressure are illustrated at a central portion 234 of the anterior end 230. Though the image of the prosthetic foot 200 in FIG. 3 uses the colors green, red and yellow to illustrate areas of different pressure, any color shade or pattern can be used to illustrate said pressures differences.

As one of ordinary skill in the art will recognize, measurement of the pressure distribution of the prosthetic foot 200 is not limited to the use of the system 100 described above and shown in FIG. 1. In another embodiment, the pressure distribution can be obtained from sensors (not shown) disposed on the prosthetic foot 200. In one embodiment, said sensors are configured to communicate a force exerted by the prosthetic foot 200 during motion to a central processing unit (not shown). The pressure distribution can then be generated as described above. In another embodiment, said sensors collect said pressure distribution data, which may later be used to generate an image of the pressure distribution of the prosthetic foot 200. The sensors 12 can comprise any suitable structure configured to sense a force applied by the prosthetic foot 200 during motion. For example, in one embodiment the sensors 12 can comprise sensing strips or sensing areas.

In the embodiment illustrated in FIG. 3, the pressure distribution comprises a plurality of dots 300, or pressure points, extending between the posterior end 220 and the anterior end 230 of the prosthetic foot 200. In one embodiment, the posterior end 220 corresponds to a heel section of the prosthetic foot 200 and the anterior end 230 corresponds to a toe section of the prosthetic foot 200.

With reference to FIGS. 1 and 3, each of the plurality of dots 300, which together define the pressure distribution, corresponds to a force reading sensed by the sensors 12 (i.e., a pressure point). Accordingly, each of the dots 300 corresponds to a reading of the sensors 12. Additionally, the pressure distribution illustrates the performance of the prosthetic foot 200. In one embodiment, the performance is defined by the spacing between the dots 300, which represents the general speed of the posterior-anterior motion or rollover of the prosthetic foot 200. As illustrated in FIG. 3, the dots 300 are generally close to each other in a first portion 310 of the pressure distribution of the foot 200, which represents a slower posterior-anterior motion or rollover of the prosthetic foot 200 in the first portion 310. In contrast, the dots 300 are generally further apart in a second portion 320 of the pressure distribution, which represents a faster rollover of the prosthetic foot 200 in the second portion 320.

One of ordinary skill in the art will recognize that the number of dots 300 in the pressure distribution for the prosthetic foot 200, e.g. in FIG. 3, depends on the measurement frequency of the system 100 and the amount of time the prosthetic foot 200 is in contact with the surface 10. For example, if the measurement frequency of the system 100 is approximately 120 Hz, and the average contact time for the prosthetic foot 200 during a walking motion is between about 0.65 and about 0.75 seconds, then the pressure distribution would include between about seventy-eight and about ninety pressure points or dots 300. In contrast, if the measurement frequency of the system 100 is approximately 350 Hz and the average contact time for the prosthetic foot 200 remains the same, the pressure distribution would include between about 227 and about 262 dots 300. Preferably, the measurement frequency of the system 100 if between about 20 and about 1000 Hz. More preferably, the measurement frequency of the system 100 is between about 50 and about 500 Hz.

With continuing reference to FIG. 3, the spacing between the dots 300 can also illustrate how smooth the rollover of the prosthetic foot 200 is. Preferably, for substantial rollover smoothness, the dots 300 at the posterior end 220, or heel section of the foot 200, are generally close together, illustrating the absorption of energy during heel strike. The dots 300 then preferably grow generally further apart as the prosthetic foot 200 moves anteriorly, illustrating a more rapid posterior-anterior motion of the prosthetic foot 200 and energy return at toe-off. In one embodiment, the dots 300 at the energy return stage are between about 10% to about 200% further apart than at the energy absorption stage. In another embodiment, the dots 300 are between about 50% and about 100% further apart than at the energy absorption stage. In still another embodiment, the dots 300 are between about 10% and about 50% further apart than at the energy absorption stage. Preferably, over the entire rollover of the foot 200, the spacing between substantially every set of two dots does not vary by more than between about 10% and about 300%, and more preferably between about 50% and about 200%, from the spacing between another set of two dots. In another embodiment, the spacing between substantially every set of two dots does not vary by more than between about 10% and about 200% from an average spacing between the dots 300, over the entire rollover of the prosthetic foot 200. A substantially smooth rollover allows for sufficient compression of the posterior end 220 to store energy, which will be returned during toe-off at the anterior end 230 of the prosthetic foot 200. Said storage and return of energy may vary between different prosthetic foot designs, as well as between users.

Figure 5:
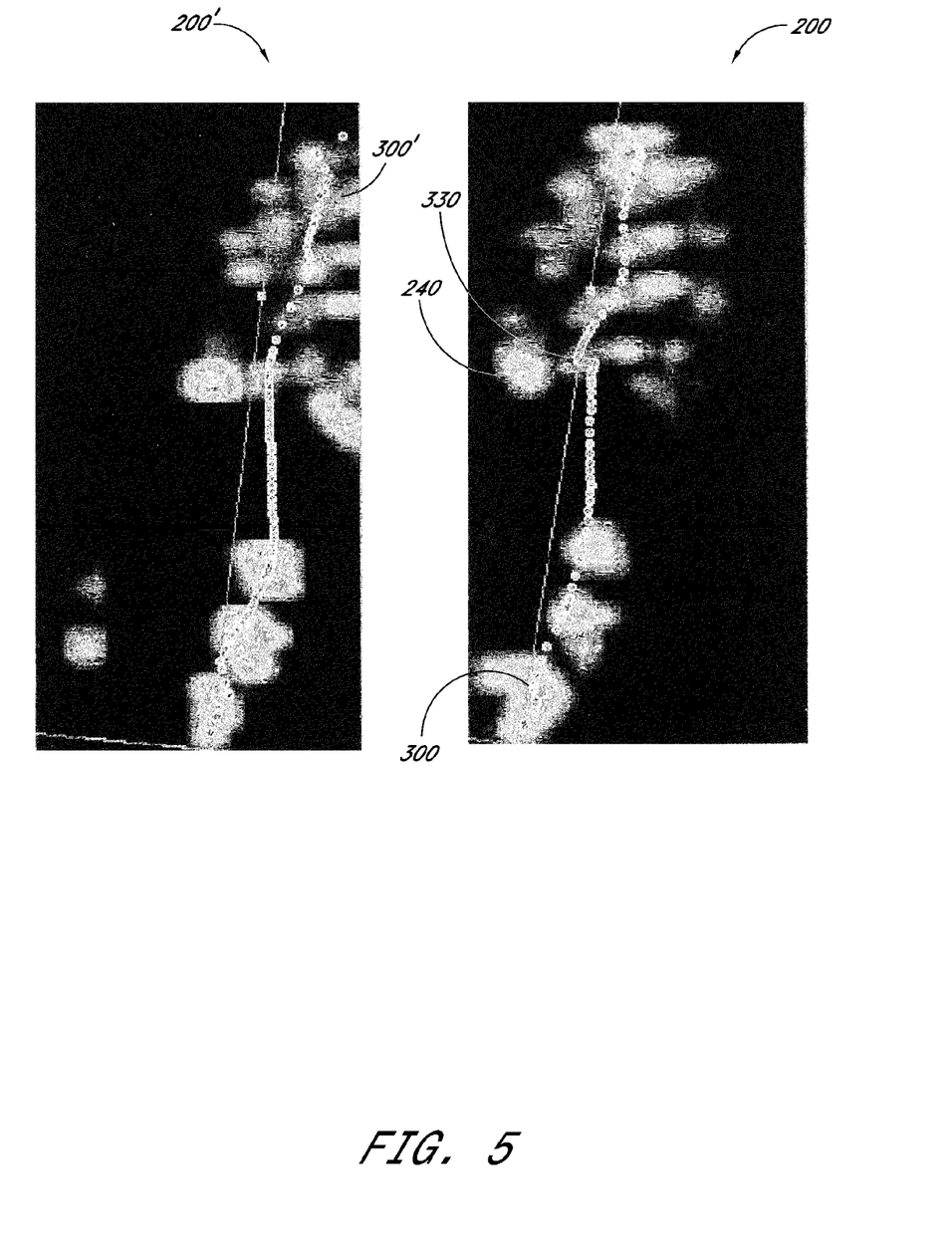
FIG. 5 is an image of two prosthetic foot designs and their corresponding pressure distributions.

With continuing reference to FIG. 3, the spacing between the dots 300 can also illustrate the degree of dorsi-flexion and plantar flexion of the prosthetic foot 200 during rollover. For example, if the prosthetic foot 200 provides significant resistance to rollover during dorsi-flexion, the dots 300 will appear substantially concentrated and may in some cases be shown to move posteriorly before moving anteriorly. Likewise, the more significant the resistance to rollover is during plantar flexion of the prosthetic foot 200, the generally closer the dots 300 are, which may even move posteriorly as described above, illustrating an interruption in the progression of rollover. As illustrated in FIG. 5 with respect to a metatarsal or forefoot region 240 of the prosthetic foot 200, such a resistance or interruption in rollover is exhibited as a discontinuity or kink 330 in the trajectory of the pressure distribution. Such significant resistance to rollover can result in added strain on a user's knee, creating a hyper-extension momentum on the knee and requiring the user to exert additional muscle force to complete the rollover of the foot 200. On the other hand, very little resistance to rollover when the forefoot region 240 touches the surface 10, which is exhibited by relatively larger spacing between the dots 300, may result in buckling of the knee, creating a flexion moment on the knee. Thus, in one embodiment, this system can be used to design a foot without such kinks 330 (e.g., substantially every dot is disposed anterior to the previous dot), or large spacing between the dots 300.

In another embodiment, the performance of the prosthetic foot 200 is illustrated by the frequency of the dots 300. For example, if the pressure distribution has very few dots 300, the rollover of the prosthetic foot 200 is generally fast. In contrast, if the pressure distribution has many dots 300, the rollover of the prosthetic foot 200 is generally slow.

Figure 4:
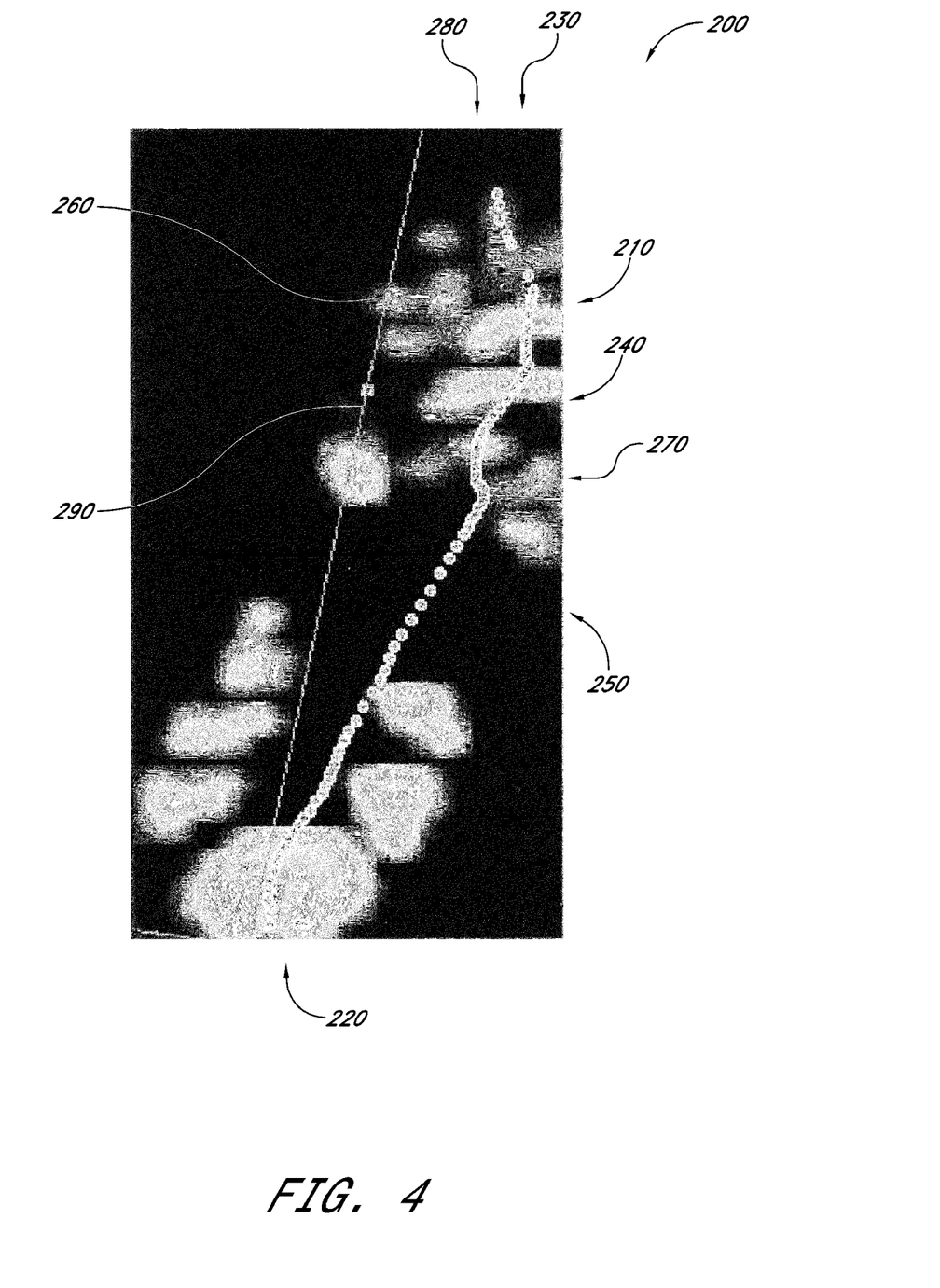
FIG. 4 is another image of a prosthetic foot.

In still another embodiment, illustrated in FIG. 4, the performance of the prosthetic foot 200 is defined by the trajectory of the pressure distribution during the rollover of the prosthetic foot 200. The prosthetic foot 200 is a right foot model, as described in U.S. Provisional Patent Application No. 60/575,142. Preferably, the trajectory of the center of pressure starts generally at the center of the posterior end 220 or heel and travels in a substantially straight line through a mid-section 250 of the foot 200 until it reaches the forefoot region 240 of the foot 200. The trajectory then preferably curves medially, or toward an inner (or medial) edge 260 of the prosthetic foot 200 and away from an outer (or lateral) edge 270 of the foot 200. The trajectory preferably continues generally toward the anterior end 230 of the prosthetic foot 200. In the illustrated embodiment, where the prosthetic foot 200 is a right foot model, the inner edge 260 of the foot 200 is the left-hand side edge, so that a medial progression of the pressure distribution corresponds to a trajectory that curves left. The lateral portion of the foot 200 is on the outer edge 270 of the foot 200 and corresponds to the right-hand side edge in a right foot model. Similarly, in an embodiment where the prosthetic foot 200 is a left foot model, the inner edge 260 is the right-hand side edge of the foot 200 and the outer edge 270 is the left-hand side edge. Accordingly, for a left foot model, medial progression of the pressure distribution corresponds to a trajectory that curves right. In one embodiment, the trajectory of the pressure distribution curves medially and continues toward a toe section 280 of the anterior end 230, corresponding generally to the location of a first and second toes on a human foot.

With reference to FIGS. 3 and 4, a reference line 290 may be used to illustrate the degree of medial-lateral motion of the pressure distribution as the foot 200 moves from the posterior end 220 to the anterior end 230. In one embodiment, the reference line 290 can be aligned, e.g., by a user operating the computer 20, along a longitudinal center of the foot 200 so that generally equal areas of the foot 200 are on either side of the reference line 290. In said embodiment, the reference line 290 thus represents an axis of the foot 200. The degree of medial-lateral motion of the foot 200 during rollover can therefore be more easily recognized and measured (e.g., via the deviation of the pressure distribution from the reference line 290). In FIG. 3, the pressure distribution has a trajectory that is substantially linear and generally coincides with the reference line 290, which illustrates the lack of medial-lateral motion of the foot 200 during rollover. However, in another embodiment the reference line 290 need not be aligned with the longitudinal center of the foot 200, as shown in FIG. 4. Here, the reference line 290 extends from the posterior end 220 toward the inner edge 260 of the foot 200, but the medial-lateral movement of the pressure distribution is readily recognizable.

The performance of the prosthetic foot 200 can be measured by comparing the pressure distribution of the prosthetic foot 200 to a desired rollover performance. In one embodiment, the desired rollover performance comprises a preselected range of performance values for the prosthetic foot 200. For example, the preselected range can consist or values for the speed of the rollover of the prosthetic foot 200, the degree of curvature for the trajectory of the pressure distribution (e.g., the degree of media-lateral motion), and the smoothness of the rollover as defined by the spacing of the dots 300 and the lack of any kinks 330 (see FIG. 5). In another embodiment, the preselected range can consist of performance values corresponding to the rollover profile of a human foot. However, the desired rollover performance can comprise other characteristics generally used in measuring the performance of a prosthesis.

In one embodiment, the pressure distribution data obtained can be used to design or redesign the prosthetic foot 200. For example, the design of the prosthetic foot 200 can be modified to approximate a desired pressure distribution or rollover profile. In one embodiment, the prosthetic foot 200 can be designed or redesigned to provide a generally straight rollover trajectory, as shown in FIG. 3. In another embodiment, the prosthetic foot 200 can be designed to provide a prosthetic foot 200 whose rollover trajectory curves first laterally and then further medially as the foot 200 moves anteriorly, as shown in FIG. 5. In another embodiment, the prosthetic foot 200 can be designed to provide slower rollover during heel-strike and toe-off. In still another embodiment, the prosthetic foot 200 can be designed to provide faster rollover in between heel-strike and toe-off. In yet another embodiment, the pressure distribution data obtained can be used to design the prosthetic foot 200 to provide a rollover profile that approximates the rollover profile of a human foot (see FIG. 6). In another embodiment, the degree of pressure exerted by the prosthetic foot 200, as illustrated by the color shades of an image of the prosthetic foot 200, can be used to design the prosthetic foot 200 to increase or lessen the degree of pressure exerted at a location of the sole 210 of the prosthetic foot 200, such as at the posterior end 220, the anterior end 230, the forefoot 240 or the mid section 250 of the foot 200. In still another embodiment, the pressure distribution data can be used to design or redesign the prosthetic foot 200 to provide a more fluid rollover between heel-strike and toe-off. Further discussion of features used in the design of a prosthetic foot to achieve a fluid rollover can be found in U.S. patent application Ser. No. 10/642,125, filed Aug. 15, 2003, which is hereby incorporated by reference in its entirety and should be considered a part of this specification.

The prosthetic foot 200 can be designed in any suitable way to achieve the desired preselected range of rollover performance values. In one embodiment, a sole 210 of the prosthetic foot 200 can be designed to achieve the desired rollover. For example, the prosthetic foot 200 can employ different materials of selected stiffness at preselected locations on the prosthetic foot 200, wherein said materials are selected to guide the rollover of the prosthetic foot 200 in a desired manner, such as to achieve a more medial-lateral progression of the center of pressure of the prosthetic foot 200. In another embodiment, the prosthetic foot 200 can comprise a foot cover (not shown), wherein the foot cover is designed to include different materials of different stiffness at preselected locations to guide the rollover of the foot 200. Further discussion of such foot cover designs and features used in the design of prosthetic feet to achieve a desired rollover performance can be found in U.S. Provisional Patent Application No. 60/575,587, filed May 28, 2004, which is hereby incorporated by reference in its entirety and should be considered a part of this specification.

As discussed above, the pressure distribution of the prosthetic foot 200 can be displayed to illustrate the performance of the prosthetic foot 200 during the posterior-anterior motion or rollover of the foot 200. In a preferred embodiment, the pressure distribution is displayed on an image of the prosthetic foot 200, as shown in FIG. 3. In one embodiment, the image of the prosthetic foot 200 includes an image of the sole 210 of the prosthetic foot 200.

In another embodiment, the pressure distribution of a second prosthetic foot 200' is also illustrated and compared to the pressure distribution of the prosthetic foot 200, as shown in FIG. 5. Preferably, the pressure distribution of the second prosthetic foot 200' is displayed on an image of the second prosthetic foot 200'. In another embodiment, the pressure distribution of the second prosthetic foot 200' can be displayed together with the pressure distribution of the prosthetic foot 200. In the illustrated embodiment, two right foot models of the prosthetic feet 200, 200' are compared; the prosthetic foot 200 is a Talux® foot by Ossur and the prosthetic foot 200' is a Luxon Max model by Otto Bock of Minneapolis, Minn. Alternatively, two left foot models, or one left foot model and one right foot model, can be compared. As illustrated in FIG. 5, the prosthetic foot 200' exhibits a more uniform distribution of dots 300 without any kinks, as discussed above.

Figure 6:
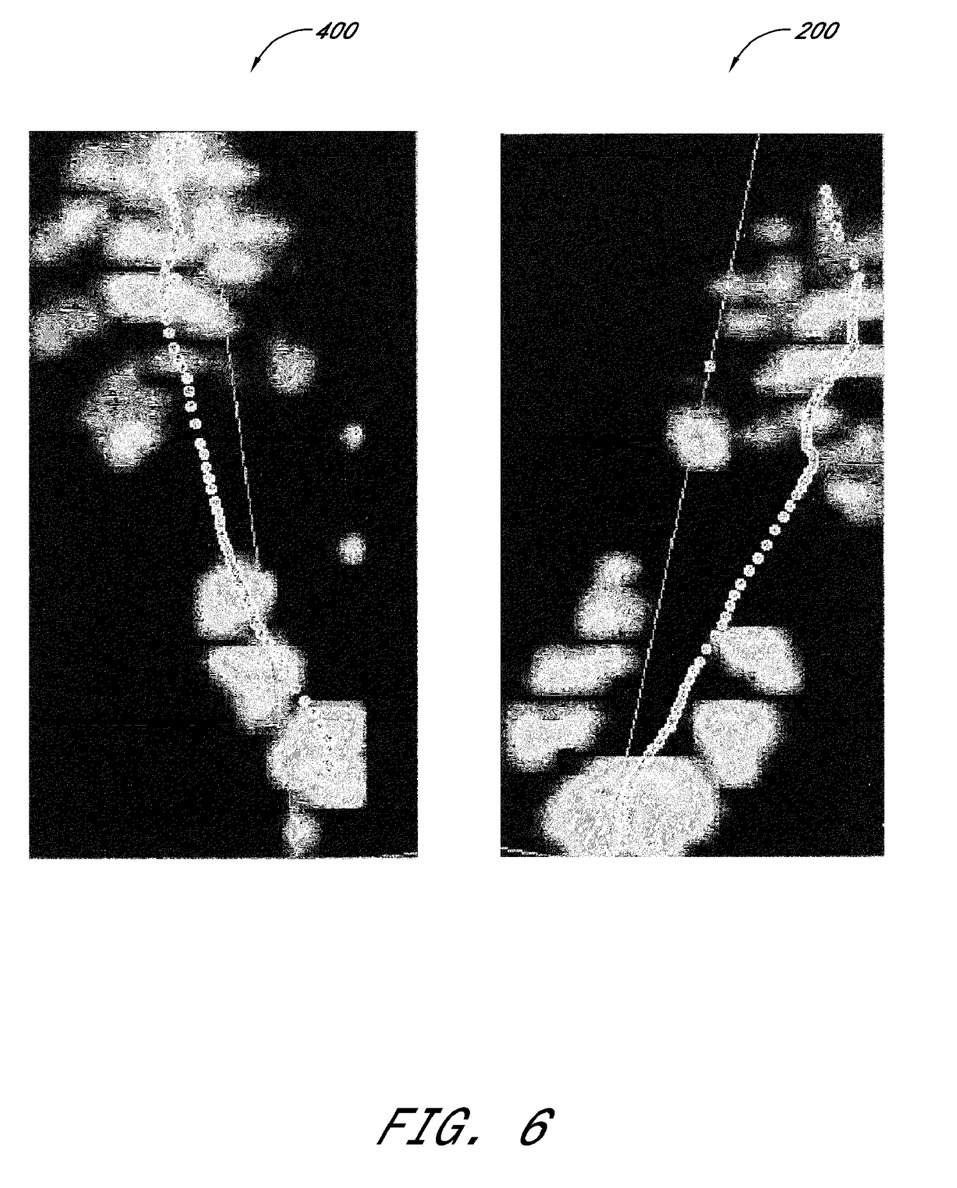
FIG. 6 is an image of a prosthetic foot and a human foot, and their corresponding pressure distributions.

In still another embodiment, the pressure distribution of a prosthetic foot 200 is compared to a pressure distribution of a human foot 400, as shown in FIG. 6. Preferably, the pressure distribution of the human foot 400 is displayed on an image of the human foot 400. In another embodiment, the pressure distribution of the human foot 400 can be displayed together with the pressure distribution of the prosthetic foot 200. In the illustrated embodiment, the image of the human foot 400 (seen on the left hand side in FIG. 6) is that of a left foot, whereas the image of the prosthetic foot 200 (seen on the right hand side in FIG. 6) is that of a right foot model of the foot design described in U.S. Provisional Patent Application No. 60/575,142. Alternatively, the human foot 400 can be a right foot and the prosthetic foot 200 can be a left foot model, or both can be right feet or left feet.

The pressure distributions generated as discussed above can be used to compare the performance of different prosthetic foot designs 200, 200', as shown in FIG. 5. Said comparison can be used in advertisements or other publications to illustrate the difference in performance between the prosthetic foot designs 200, 200'. For example, the pressure distribution trajectory for each of the designs 200, 200' can be generated or obtained and compared with each other, as shown in FIG. 5. In one embodiment, said comparison can be displayed as discussed above to illustrate the difference in performance of the prosthetic foot designs 200, 200' relative to each other. A user can then determine, based on said comparison, which of the designs 200, 200' has a superior performance. For example, the user can compare the pressure distribution trajectories for the prosthetic foot designs 200, 200' to determine which design has the better medial-lateral motion. Additionally, the user can compare the distance or spacing between the dots 300, 300', or pressure points, of the pressure distribution trajectories for the prosthetic foot designs 200, 200' to determine which design provides the smoother rollover. Also, the user can compare the frequency of the dots 300, 300' of the pressure trajectories for the prosthetic foot designs 200, 200' to determine which design has the faster rollover.

In another embodiment, the pressure distribution generated as discussed above can be used to compare the performance of a prosthetic foot relative to a human foot. For example, the pressure distribution trajectory for the prosthetic foot 200 can be generated or obtained and compared with the pressure distribution for the human foot 400, as shown in FIG. 6. In one embodiment, said comparison can be displayed as discussed above to illustrate the performance of the prosthetic foot 200 relative to the human foot 400. A user can then determine, based on said comparison, the performance of the prosthetic foot 200 relative to the human foot 400. For example, the user can determine how closely the medial-lateral motion of the prosthetic foot 200 approximates the medial-lateral motion of the human foot 400. Additionally, the user can determine how closely the posterior-anterior motion of the prosthetic foot 200 approximates the posterior-anterior motion of the human foot 400. Also, the user can compare the smoothness or quickness of the rollover in the manner discussed above. Additionally, the prosthetic foot 200 could be assigned a performance rating based on the performance of the prosthetic foot 200 relative to the rollover profile of the human foot 400.

All of these aspects are intended to be within the scope of the invention herein disclosed. These and other aspects of the present invention will become readily apparent to those skilled in the art from the appended claims and from the preceding detailed description of the preferred embodiments having reference to the attached figures, the invention not being limited to any particular preferred embodiment(s) disclosed.

What is claimed is:

1. A method of measuring prosthetic foot gait characteristics, comprising:
obtaining a pressure distribution of a prosthetic foot during motion of the prosthetic foot, wherein the pressure distribution comprises a trajectory of center of pressure values obtained during rollover of the prosthetic foot ; and
storing the pressure distribution of the prosthetic foot in a storage medium.

2. The method of claim 1, wherein the pressure distribution is measured using a surface incorporating a plurality of sensors, wherein the prosthetic foot moves over the surface, said sensors sensing a force exerted by at least a portion of the prosthetic foot on the surface, the sensors communicating said sensed force to a computer.

3. The method of claim 1, further comprises displaying the stored pressure distribution as an image through an output device.

4. The method of claim 3, wherein the image comprises an image of a sole of the prosthetic foot and the pressure distribution.

5. The method of claim 4, further comprises displaying a second pressure distribution of a second prosthetic foot as a second image.

6. The method of claim 5, wherein the second image comprises an image of a sole of the second prosthetic foot and the second pressure distribution.

7. The method of claim 3, further comprises displaying a second pressure distribution of a human foot.

8. The method of claim 7, wherein the pressure distribution of the human foot is displayed on an image of the human foot.

9. The method of claim 3, wherein displaying the pressure distribution includes displaying a trajectory of the pressure distribution, wherein the smoothness of the trajectory demonstrates the performance of the prosthetic foot.

10. The method of claim 3, wherein displaying the pressure distribution includes displaying a plurality of pressure points, wherein the frequency of the pressure points demonstrates the performance of the prosthetic foot.

11. The method of claim 3, wherein displaying the pressure distribution includes displaying a plurality of pressure points, wherein the spacing of the pressure points demonstrates the performance of the prosthetic foot.

12. The method of claim 1, wherein the stored pressure distribution approximates a desired pressure distribution corresponding to a range of rollover performance values.

13. The method of claim 1, further comprising designing a prosthetic foot so that the stored pressure distribution approximates a desired pressure distribution corresponding to a range of rollover performance values.

14. The method of claim 1, further comprising manufacturing a prosthetic foot so that the stored pressure distribution approximates a desired pressure distribution corresponding to a range of rollover performance values.

15. The method of claim 1, wherein the obtaining the pressure distribution further comprises generating a center of pressure profile.

16. The method of claim 1, wherein the stored pressure distribution substantially approximates a rollover of a natural human foot.

17. The method of claim 1, wherein the stored pressure distribution comprises a range of rollover performance values comprising a desired range of anterior-posterior motion.

18. The method of claim 1, wherein the stored pressure distribution comprises a range of rollover performance values comprising a desired range of medial-lateral motion.

19. The method of claim 1, comprising obtaining a frequency of pressure points in the pressure distribution.

20. The method of claim 1, wherein the stored pressure distribution comprises a range of rollover performance values defined by a smoothness of a trajectory of the pressure distribution.

21. A method of measuring a prosthetic foot, comprising:
obtaining a pressure distribution of a prosthetic foot during motion of the prosthetic foot, wherein the pressure distribution comprises a trajectory of center of pressure values obtained during rollover of the prosthetic foot, and
redesigning or modifying the prosthetic foot for a user of the prosthetic foot based on the pressure distribution.

22. The method of claim 21, wherein the redesigning or modifying of the prosthetic foot is further based on comparing the pressure distribution to a desired pressure distribution stored in a storage medium.

23. The method of claim 21, wherein the redesigning or modifying the prosthetic foot is performed during manufacturing of the prosthetic foot.

24. The method of claim 2, wherein the surface incorporating a plurality of sensors is decoupled from the prosthetic foot.

25. The method of claim 23, wherein the redesigning or modifying of the prosthetic foot is further based on comparing the pressure distribution to a desired pressure distribution stored in a storage medium.

* * * * *